US012758714B2

(12) United States Patent
Webb et al.

(10) Patent No.: US 12,758,714 B2
(45) Date of Patent: Oct. 13, 2026

(54) AUTOMATIC NEEDLE-FREE INJECTOR CONTAINER UNIT SYSTEM

(71) Applicant: Vaccination Kiosks, LLC, Rockwall, TX (US)

(72) Inventors: Keith Webb, Rockwall, TX (US); Karim Menassa, Saint-Laurent (CA); Maurice Menassa, Pierrefonds (CA); Adam Gadoua, Laval (CA); Charles Ibrahim Khairallah, Verdun (CA)

(73) Assignee: Vaccination Kiosks, LLC, Rockwall, TX (US)

( * ) Notice: Subject to any disclaimer, the term of this patent is extended or adjusted under 35 U.S.C. 154(b) by 426 days.

(21) Appl. No.: 18/549,999

(22) PCT Filed: Mar. 11, 2022

(86) PCT No.: PCT/US2022/019891
§ 371 (c)(1),
(2) Date: Sep. 11, 2023

(87) PCT Pub. No.: WO2022/192632
PCT Pub. Date: Sep. 15, 2022

(65) Prior Publication Data

US 2024/0165334 A1 May 23, 2024

Related U.S. Application Data

(60) Provisional application No. 63/160,095, filed on Mar. 12, 2021.

(51) Int. Cl.

| | |
|---|---|
| ***A61M 5/30*** | (2006.01) |
| ***A61M 5/20*** | (2006.01) |
| *A61D 1/02* | (2006.01) |

(52) U.S. Cl.
CPC ................ *A61M 5/30* (2013.01); *A61M 5/20* (2013.01); *A61D 1/025* (2013.01);
(Continued)

(58) Field of Classification Search
CPC .... A61M 5/30; A61M 5/427; A61M 2205/14; A61D 1/025; A61D 7/00; G06Q 20/18; G16H 20/17
See application file for complete search history.

(56) References Cited

U.S. PATENT DOCUMENTS 4,342,310 A 8/1982 Lindmayer
4,623,332 A 11/1986 Lindmayer
(Continued)

OTHER PUBLICATIONS

International Search Report dated May 18, 2022 in parent International application PCT/US2022/019891.
(Continued)

*Primary Examiner* — Laura A Bouchelle
(74) *Attorney, Agent, or Firm* — Polson Intellectual Property Law, PC; Margaret Polson

(57) ABSTRACT

An automatic needle-free injector container unit system is provided. The system comprises a needle-free injector for injecting a medicament from a cartridge to a user, such as a human or small pet, wherein the needle-free injector comprises a cartridge chamber for receiving the cartridge; and an injector movement mechanism for automatically and reversibly positioning the needle-free injector to one or more of: a home position where injector is retracted and positioned away from contact with the user, and an injecting position where the injector is in proximity' to the user for injection of the medicament; and a container for housing the needle-free injector and injector movement mechanism. One or more sensors may also be provided to facilitate the injection process. The system may be a portable unit and located,
(Continued)

remotely from medical facilities, and controlled locally and/or remotely by a user with a computer interface.

13 Claims, 18 Drawing Sheets

(52) U.S. Cl.
CPC . *A61M 2005/2006* (2013.01); *A61M 2205/14* (2013.01); *A61M 2205/33* (2013.01); *A61M 2205/502* (2013.01)

(56) References Cited

U.S. PATENT DOCUMENTS

| | | | | |
|---|---|---|---|---|
| 4,758,227 | A * | 7/1988 | Lancaster, Jr. | A61D 1/025 604/144 |
| 7,357,915 | B2 | 4/2008 | Menassa | |
| 7,850,665 | B2 * | 12/2010 | Johnston, Jr. | A61M 5/20 604/272 |
| 8,066,662 | B2 * | 11/2011 | Azar | A61M 5/30 604/71 |
| 8,172,790 | B2 | 5/2012 | Hunter et al. | |
| 8,821,424 | B2 | 9/2014 | Hunter et al. | |
| 9,067,019 | B2 | 6/2015 | Menassa | |
| 9,067,020 | B2 | 6/2015 | Menassa | |
| 9,308,326 | B2 | 4/2016 | Hunter et al. | |
| 9,498,407 | B2 | 11/2016 | Menassa | |
| 9,662,460 | B2 | 5/2017 | Menassa | |
| 2018/0068088 | A1 | 3/2018 | Webb | |
| 2021/0077728 | A1 * | 3/2021 | Anquetil | A61M 5/19 |

OTHER PUBLICATIONS

Written Opinion of the International Searching Authority dated May 18, 2022 in parent International application PCT/US2022/019891.

* cited by examiner

SECTION A-A

SECTION B-B

FIG. 12B
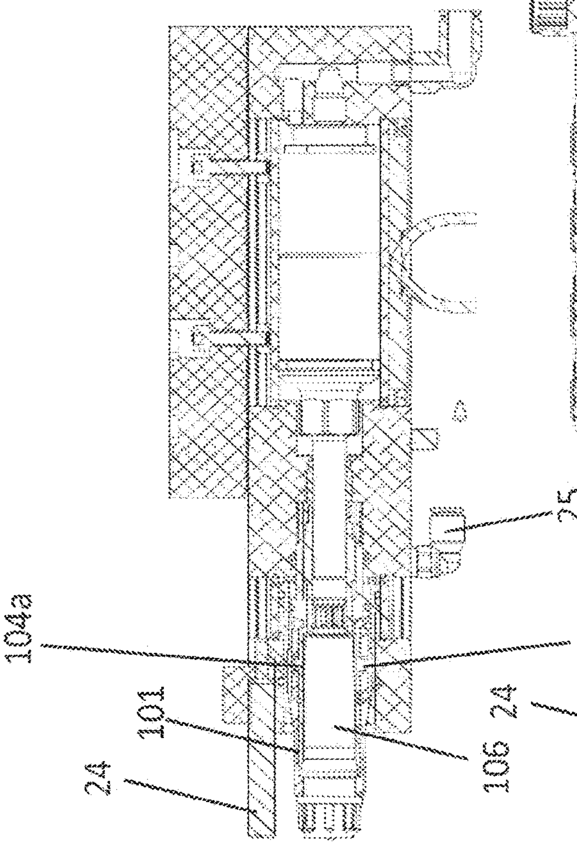
FIG. 12D
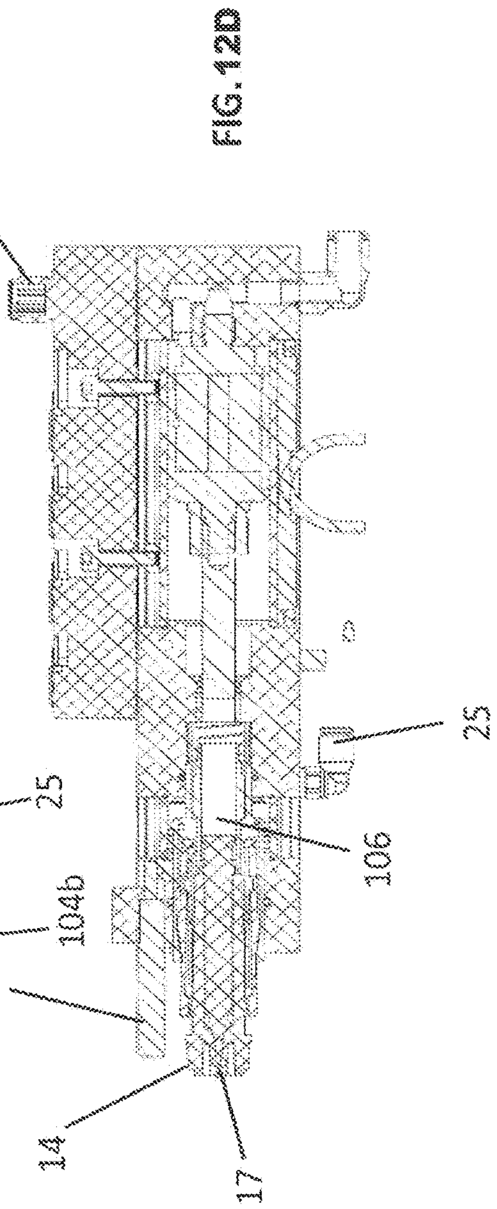
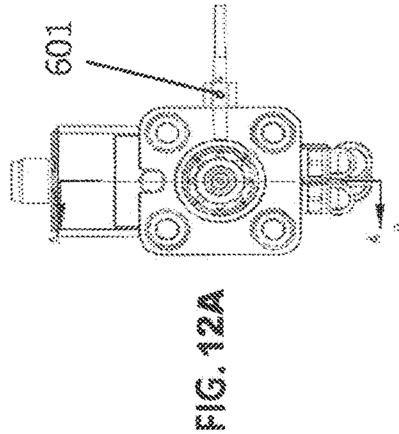
FIG. 12A
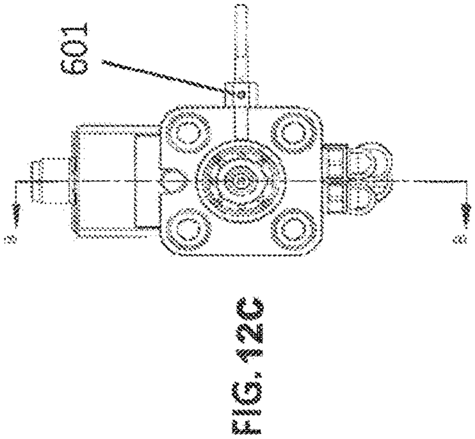
FIG. 12C

AUTOMATIC NEEDLE-FREE INJECTOR CONTAINER UNIT SYSTEM

CROSS REFERENCE TO RELATED APPLICATION

This application claims priority to U.S. Provisional Patent Application 63/160,095, filed Mar. 12, 2021, the entire contents of which are incorporated by reference herein.

FIELD

The present application generally relates to a medical injector, and more particularly to an automatic needle-free injector system for automatically injecting a medicament into a person or animal in need thereof, and a portable container unit comprising said automatic injector and system.

BACKGROUND

Needle-free injectors and accessories thereof are known in the art (see, for example, U.S. Pat. No. 7,357,915 to Menassa; U.S. Pat. No. 9,662,460 to Menassa; U.S. Pat. No. 9,498,407 to Menassa; U.S. Pat. No. 9,067,020 to Menassa; U.S. Pat. No. 9,067,019 to Menassa; U.S. Pat. No. 4,623,332 to Lindmayer; U.S. Pat. No. 4,342,310 to Lindmayer). Such injectors typically include a chamber within a barrel for receiving or storing a medicament at a proximal (injecting) end, and a plunger and piston combination positioned at a rear (distal) end of the barrel which acts under pressure by compressed gas behind the piston. On actuation of a trigger or button, the gas is released with sufficient force to act against the piston and expel the medicament, out of the barrel through an orifice at a tip of the opposite proximal end of the chamber, and through the skin of a user (human or other animal) intending to receive the medicament. Injectors can be single-use (i.e., a single medicament for administration to a single user), but others may be reusable once the medicament has been dispensed.

Liquid medicament for a needle-free injector can be stored in a syringe external to the needle-free injector, such as shown in U.S. Pat. No. 9,498,407 supra. The liquid is discharged from the syringe through a tube into the chamber prior to injection through the orifice. In other injectors, a cartridge containing the medicament is added to the chamber. Many cartridges are typically disposable after a single use. For health and safety reasons, as well as convenience, disposable single-use cartridges are ideal to reduce cross-contamination between different users.

While the operation of a needle-free injector may be typically straightforward, it is more ideal, and can be safer, for an injection to be made by a user who has a certain degree of expertise with handling such injectors. Such skilled users would typically have knowledge of the preferred placement of the injector tip on the skin of a patient (e.g. injector angle, force, distance, etc.) and operation of the injector device itself, to ensure safe and efficient delivery of medicament. Many users prefer to have a trained medical professional administer the medicament to themselves or to an animal (such as their pet, including dogs or cats and the like) for these reasons. However, it is often inconvenient or difficult for a patient to locate such a trained professional and/or visit a doctor's office (or veterinarian, in the case of a pet) to have the medicament injected. Thus, it would be ideal to have a means for obtaining a safe medical injection without the need for intervention by a medical professional.

Medical kiosks are becoming more common. Such kiosks are typically standalone devices (e.g. table or desktop computers or floor model interactive computer screens, etc.) which offer medical information and services for patients, in the absence of a physical medical professional present. These kiosks can be used at the convenience of the user, usually without booking a prior appointment. A user can obtain general or specific health and medical information, purchase medicine, or have a virtual appointment through a video stream with a medical professional remotely.

Webb, US patent publication 2018068088, describes a kiosk for allowing a user to vaccinate their pet (such as a dog or cat). The kiosk has a "gun-type" needle-free jet injector where a customer purchases a dose of medication which is stored in the kiosk (such as in a refrigerated unit within the kiosk). The customer then places their pet animal on a platform or table within the kiosk. A jet injector is located in a compartment within the kiosk, and is connected to the interior of the kiosk by hoses; in operation, the jet injector is pulled out of the compartment by the user to the length allowed by the hoses. The customer then injects their animal pursuant to instructions in the kiosk. After use, the user adjusts the nozzle on the injector which allows the cartridge to fall out of or otherwise removed from the injector. The hoses are threaded back through the compartment and the injector is placed back into compartment in preparation for the next customer. As this type of injector and kiosk unit requires significant customer intervention, improper use of the injector could lead to the vaccine being improperly administered, particularly if the user fails to properly secure the cartridge within the injector. Further, improper use may compromise the cleanliness and integrity of the injector and associated equipment.

There is a need for a simpler and easy-to-use needle-free injector that can be readily used by customers outside of a medical professional facility for automatically administering a vaccine or other medicament, to themselves or to their pets.

This background information is provided for making information believed by the applicant to be of possible relevance to the present application. No admission is necessarily intended, nor should be construed, that any of the preceding information constitutes prior art against the subject matter presented herein.

SUMMARY

An aspect of the invention is to provide a novel automatic needle-free injector system, which can be used in a self-contained customer-accessible container unit for delivering medicament or vaccination to a human or an animal, including small pets.

In accordance with one aspect, the present application provides a system comprising a container unit for use in automatically administering an injection of a medicament or vaccination using a needle-free injector, the container unit comprising a housing, a needle free injector, automatic robotic mechanism, air compressor, and processor. A needle-free injector comprising one or more sensors for detecting the presence or absence of a single-use cartridge and associated means for locking the cartridge into position are also provided.

Thus, in accordance with one aspect, the present application provides an automatic needle-free injector container unit system comprising: a needle-free injector for injecting a medicament from a cartridge to a user, wherein the needle-free injector comprises a cartridge chamber for receiving the cartridge; and an injector movement mechanism for automatically and reversibly positioning the needle-free injector to one or more of: a home position where injector is retracted and positioned away from contact with the user, and an injecting position where the injector is in proximity to the user for injection of the medicament; and a container for housing the needle-free injector and injector movement mechanism. The automatic needle-free injector container unit system may further comprise a computer processor in connection with a user interface for controlling the needle-free injector and injector movement mechanism.

The cartridge comprises a medicament for injection by the needle-free injector, such as a vaccine or other medicine.

The needle-free injector as described herein may comprise one or more sensors. For example, in some embodiments, these can include a first sensor which is a jaw lock sensor that detects whether a cartridge is locked into the cartridge chamber; and/or a second sensor which is an air cylinder actuator sensor that detects when a cartridge has been inserted into the cartridge chamber. A third sensor may also be provided, which in one embodiment is a magnetic sensor which detects a position of a piston that moves forward when injecting the medicament from the cartridge.

The needle-free injector may comprise a cartridge gripper which has one or more jaw blades, wherein on insertion of a cartridge within the cartridge sensor, the air cylinder actuator sensor triggers the one or more jaw blades of the cartridge gripper to grip around the cartridge to secure it within the cartridge chamber.

In some embodiments, the automatic needle-free injector container unit system may comprise a horizontal arm having the injector thereon for moving the injector from the first position to the second position, and vice versa. In some embodiments, the container unit system comprises a storage cabinet, preferably lockable, for holding the medicament. The storage cabinet may be temperature controlled (e.g. refrigerated).

In some embodiments, there may be provided a user interface in communication with the computer processor for allowing a user to input information on the human or pet to be given the medicament, e.g. vaccinated.

The present application also provides a needle-free injector which can be used with the automatic needle-free injector container unit system as described herein.

In some embodiments, the needle-free injector container unit system may be provided in or connected with a structure e.g. a kiosk, such as a portable kiosk, to provide a self-contained location where the medicament may be administered.

A portable, remotely-located container unit comprising an automatic needle-free injector mechanism and assembly as described herein, is particularly advantageous for vaccinating humans and animals, typically small animals including dogs and cats, conveniently in the absence of direct medical supervision, and can be performed outside of and/or distant from a medical facility. The automatic needle-free injector in the container unit may be used for administering a medicament or vaccine to such a human or animal by a user who may not have medical or other training, have challenges which make it physically difficult to use an injector and/or otherwise may not have immediate access to a medical professional. Thus, the needle-free injector and container unit may be used by a wider variety of customers.

Advantageously, the present invention provides for automatic injection of a medicament or vaccine to a human or animal using an automatically controlled robotic arm mechanism that is controlled to align and position the injector in a more preferred, ideally safer and effective location than other needle-free injectors which are not used by a trained professional. Further, the use of sensors on the injector ensure that the medicament or vaccine cartridge is secured within the needle-free injector and reduces the risk of having the cartridge become undesirably expelled from the injector. In addition, the retraction of the injector after use reduces the likelihood of damage and contamination by multiple users.

BRIEF DESCRIPTION OF THE DRAWINGS

FIG. 2 shows an exemplary needle-free injector of the present application, such as shown in FIG. 1. FIG. 2A shows a front view of the injector and FIG. 2B shows a cross section of FIG. 2A along A-A, while

FIG. 6 shows different views of a container unit as described herein.

FIGS. 11-16 show various aspects and embodiments of the present invention.

DETAILED DESCRIPTION

Figure 1:
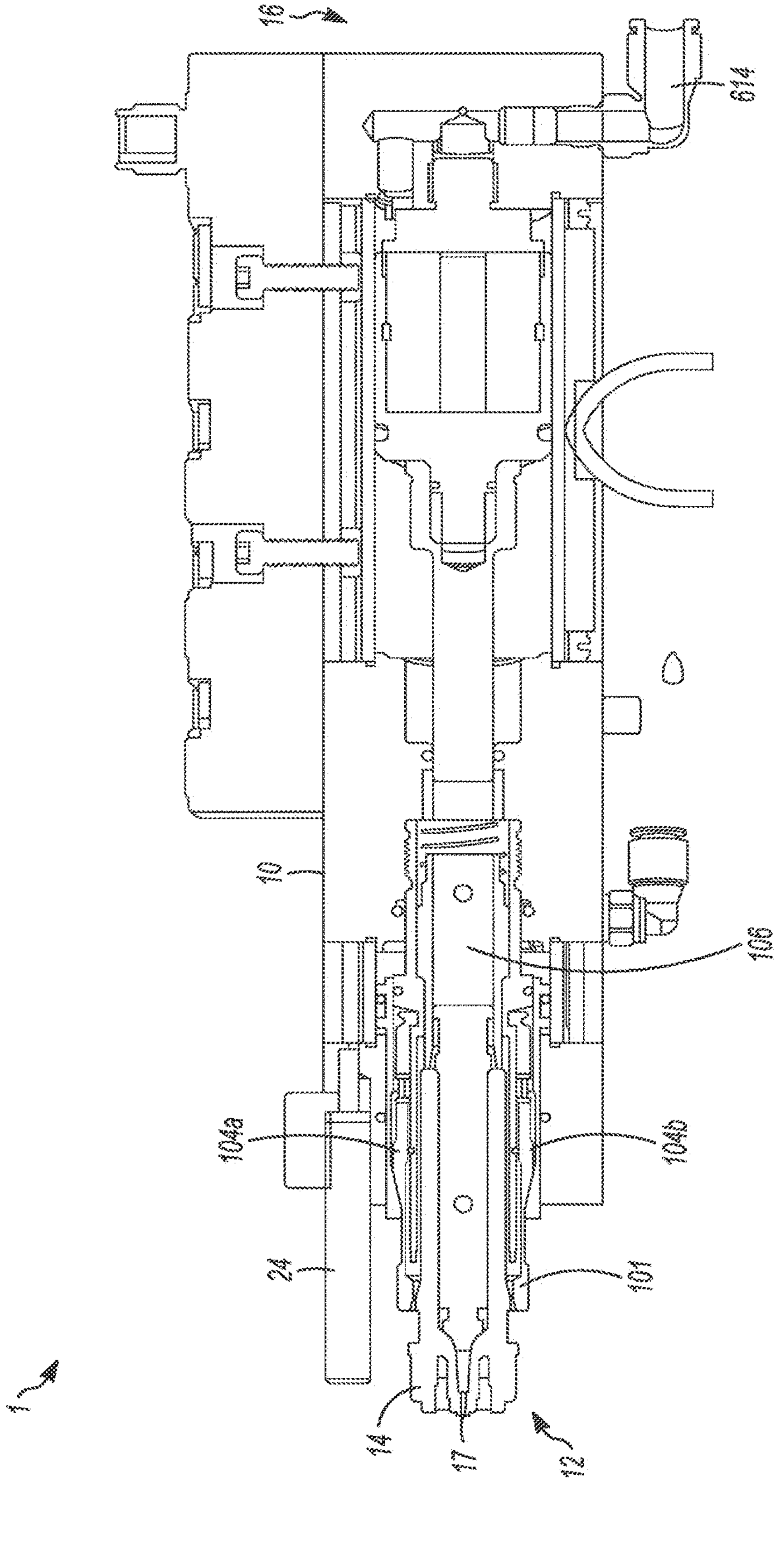
FIG. 1 shows a cross section of an exemplary needle-free injector of the present application.

In one aspect, the present application provides a portable, automatic needle-free injector and container unit system for self-administration of a medicament, such as a vaccine, to a human or animal (e.g. dog or cat), using a needle-free injector. The container unit may be standalone or integral with or attached to a kiosk, and may further comprise a compartment (such as a refrigerated unit) for storing medicaments (such as a vaccine) which are provided in vials (including cartridges), pills, capsules, or other dosage forms, and a housing for placement of the human or animal to be vaccinated using an automatically controlled needle-free injector using a robotic arm and sensor system. The container unit ideally comprises automatic ("robotic") arms and sensors for extending the injector to a position suitable for injecting the vaccine, facilitating the safe insertion of a vaccine cartridge by a user, and automatically retracting the injector within the container unit to safely dispose the expended cartridge and protect the injector for future use. An air compressor may also be provided to facilitate the injection of the medicament from the cartridge.

Existing needle-free technology for self-administration at a remote location is limited. The present container unit and modified needle-free injector and associated automatic mechanism represent a novel and unprecedented means for customers to maintain the health of their pets. The use of a remotely-located injector is particularly advantageous in times of public health emergencies, such as during the COVID-19 pandemic, where access to medical facilities may be limited, restricted or non-existent.

As used herein and unless otherwise qualified, "automatic" injection refers to a system for administering a vaccine whereby movement of the needle-free injector is controlled electronically. A needle-free injector as used herein may be attached to and controlled by a robotic arm (or the like) within the container unit, and which may be calibrated to administer the medicament or vaccine at a suitable angle and force based on information provided by the user regarding the person or animal to be injected. The robotic arm is typically controlled electronically upon activation by the user as described below and its use is facilitated by one or more sensors.

As used herein and unless otherwise qualified, the term "medicament" includes a medicine. The medicament is typically in liquid form (reconstituted or otherwise), which can be administered (injected) to a human or animal. Medicaments in other dosages forms, such as tablets or capsules, for example, may also be included. In some embodiments, the medicament is a vaccine. The words "vaccine" and "vaccination" as used herein are not intended to be limited to a vaccine per se, but could also include any other suitable medicament (or administration of said medicament), and thus may be used interchangeably with the term "medicament", unless otherwise specified. It will be appreciated that some other medicaments may require professional (e.g., medical or veterinary) supervision; these should only be administered by, or in the presence of, such trained professional, and may not be suitable for remote, self-administration use by an untrained user for safety reasons.

As used herein, "remote" or "remote location" when used to refer to injection by a user, may include the use of a needle-free injector at a location which is outside of and/or distant from: a) a medical professional normally engaged for administering a medicament, and/or b) a facility (e.g. office, clinic or laboratory, etc.) in which said professional is usually located. As used herein, "self-service" or "self-administered/self-administration" injection or vaccination includes administering a medicament to the human or animal in need of such medicament on the instructions of a user (e.g. through a computer, smartphone app or other electronic means) to the animal at that remote location, typically without the need of a medical professional physically present.

As used herein, a "pet", "animal", and "small animal" typically includes any small, usually non-aquatic animal normally kept as a pet in household settings. Typical pets of this sort include small dogs, domesticated house cats, other small mammals, rodents (e.g., gerbils, hamsters, mice, etc.), reptiles or amphibians (e.g., lizards, turtles, etc.), for example. Ideally, in the context of the present application, the injector container unit described herein may be more suited to such small animal pets, rather than larger animals (e.g., farm animals, including livestock or wild animals, etc.), but modifications may be made to the present system for such applications as desired to accommodate larger animals.

There exist concerns with securely and safely retaining cartridges in needle-free injectors, particularly for users who are not sufficiently trained with using such injectors. Cartridges which are used with needle-free injectors should be held securely during the injection process. Some existing injectors do not adequately hold the cartridges in place, which causes the cartridge to "fly out" of the injector after use. This can cause injury to the user or animal, and can also cause damage to the injector and/or the surrounding area.

The automatic needle-free injector and container unit therefor as described herein provides the user with a cartridge to insert into the injector. The injector comprises a locking mechanism (gripper assembly) for securing the cartridge within the injector. Advantageously, the locking mechanism in the injector reduces the tendency for jams, particularly in the presence of high forces necessary to achieve effective vaccine injection. For example, a typical injection itself under high pressure may undesirably expel the cartridge out prematurely or forcefully. The present cartridge locking mechanism is particularly suitable for preventing the cartridge from flying out of its location which could cause injury to the user and/or animal being vaccinated.

In one embodiment, the needle-free injector as described herein typically comprises a locking mechanism (gripper assembly) having a locking sleeve. One or more jaw blades extending therefrom secure a cartridge into position. The locking sleeve is structured to securely hold the cartridge in place. The blades are angled on the inside and the cartridge has a mating angle allowing it to rest surface-to-surface and remain held. Without wishing to be bound by theory, it has been found that as the angle approaches 90 degrees relative to the centre-line of the assembly, the amount of radial force exerted by the cartridge decreases. Ideally, the cartridge should have the same angle as the jaw blade(s). A lead-in chamfer is added to the back of the edge lock body to facilitate O-ring placement. The ring is tapered so that it can be pushed harder to apply to a slight preload. Ideally, the angle of the undercut on the jaw blade(s) is selected so that the jaw blades start to flex enough that the cartridge is suitably released therefrom.

Figure 4:
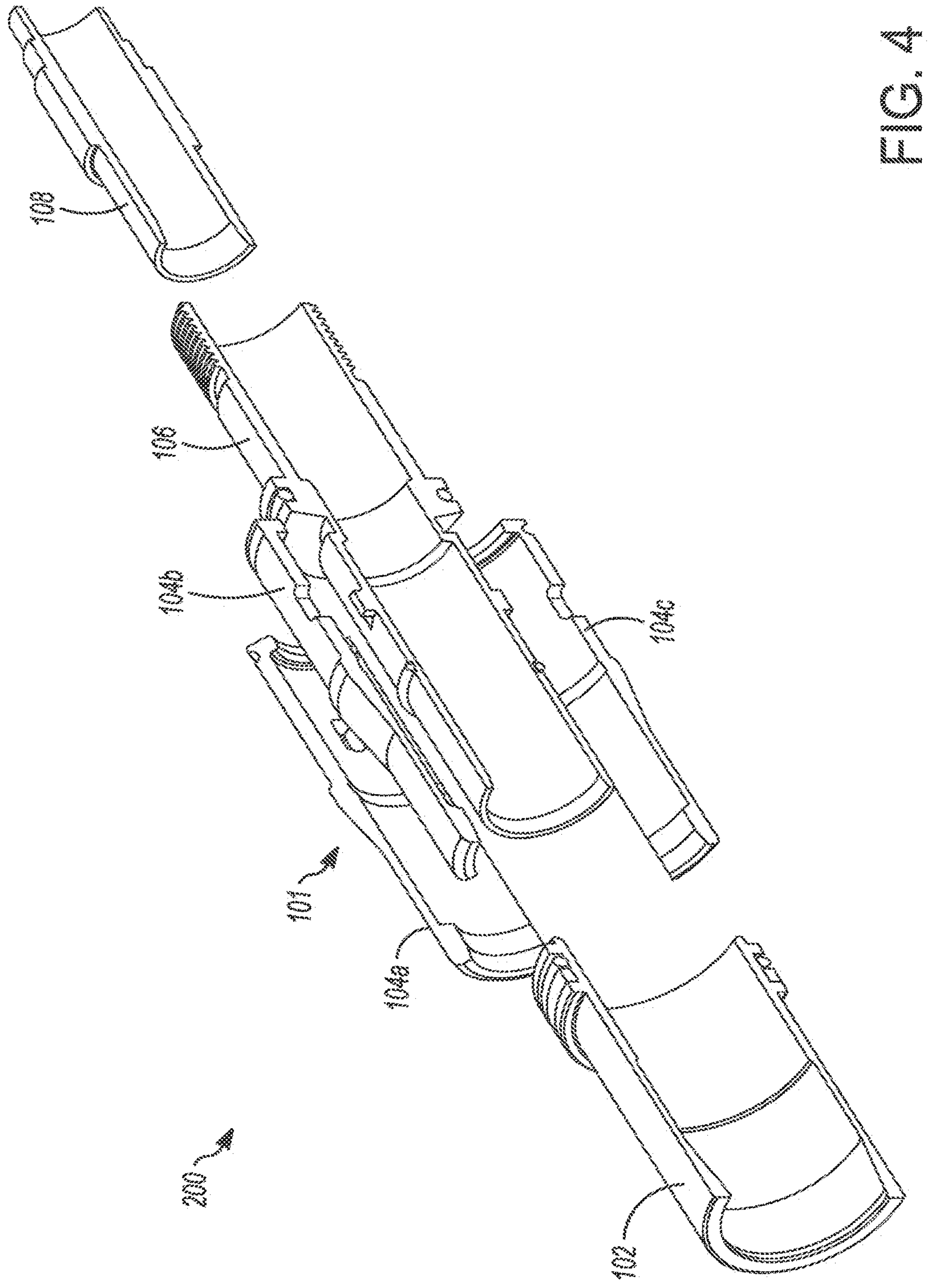
FIG. 4 shows a view, in isolation, of a lock sleeve (gripper) as used in a needle-free injector of the present application.

FIG. 1 shows a cross-section along the long axis of one embodiment of the needle-free injector. The injector 1 comprises a generally square body 10 having a generally cylindrical core, a proximal end 12 (front) where a cartridge 14 is insertable, and a distal end 16 (rear) having a gas source (or connected to a gas source, compressor) for propelling the medicament out of the tip 17 of the cartridge at the proximal end. At the proximal end 12 of the injector 1 is a cartridge chamber 106 for inserting a single-use disposable fluid medicament cartridge. In one embodiment, an auto-disabling single shot disposable cartridge may be used. However, other types and sizes of cartridges may be contemplated depending on the diameters and lengths of the cartridge chamber. The cartridges may have a volume of 0.5 mL, 1 mL or other size, and may be used for human and/or animal applications. The cartridge 14 is retained in the cartridge chamber 106 generally by a lock sleeve gripper assembly 101 having one or more gripper jaw blades 104*a*, 104*b*, 104*c* which are spring-biased or otherwise forcibly moveable. The gripper assembly 101 is double-acting to permit the jaw blades from locking and unlocking around the cartridge. An example of a gripper assembly 101 is generally illustrated in FIG. 4 and its use is described in more detail below.

Figure 2B:
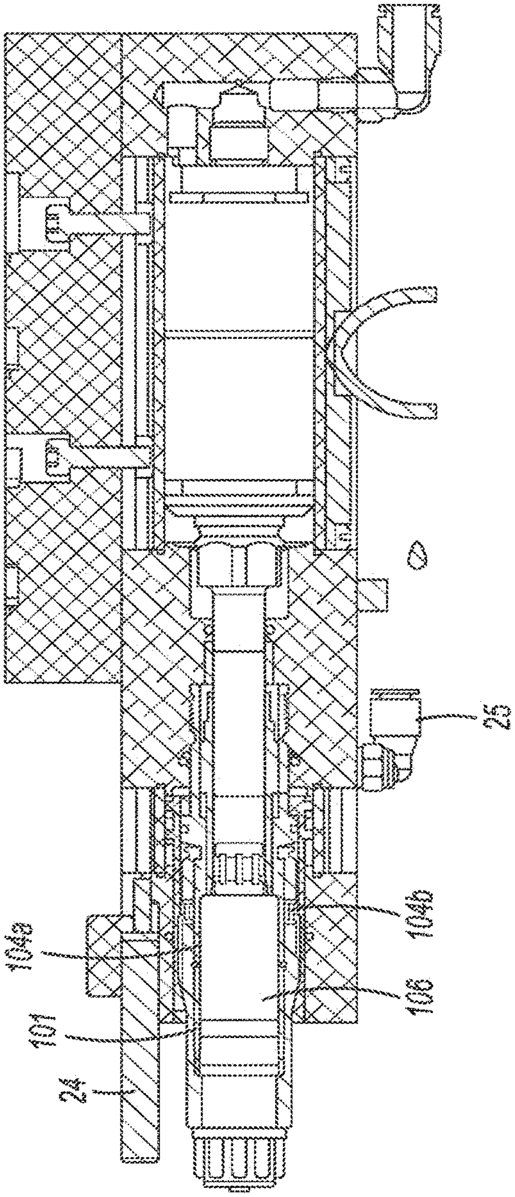
Figure 2A:
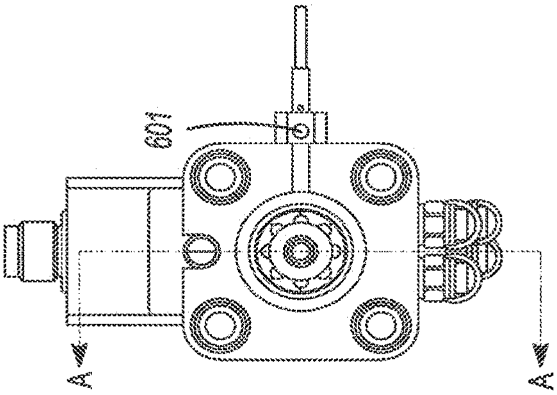
Figure 2D:
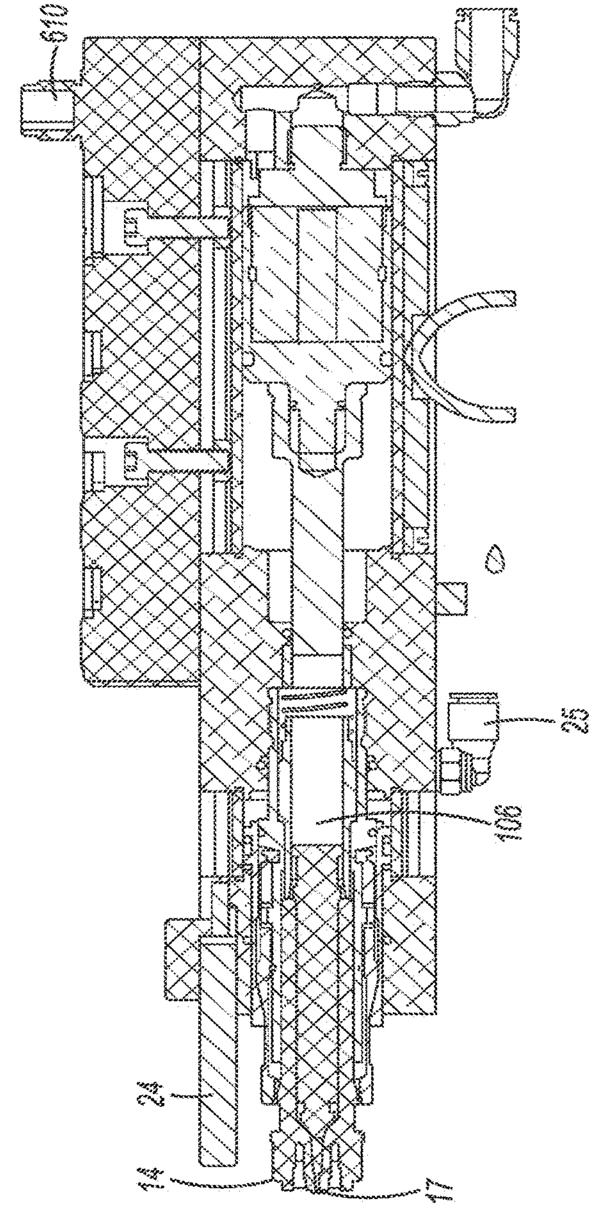
FIG. 2C shows a front view and FIG. 2D shows a cross section of FIG. 2C along B-B.
Figure 2C:
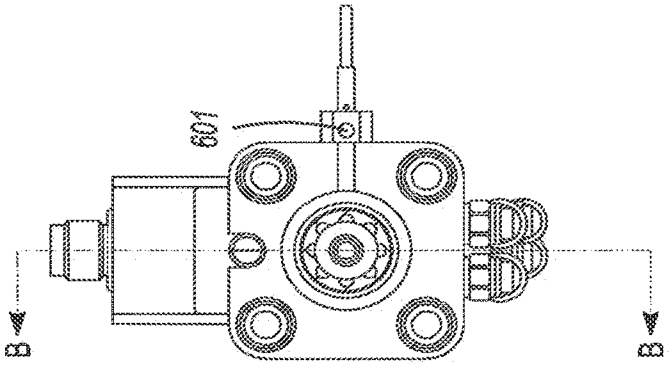

The cartridge chamber generally exists in two positions, locked and unlocked. As shown in FIG. 2A and cross-section FIG. 2B, in the locked position, the cartridge is fully inserted into the injector and the gripper assembly is closed (i.e., the gripper jaw blades 104*a-c* are engaged with the cartridge in the locked position, locking the cartridge into place). In the unlocked position, as shown in FIG. 2C and its cross-section FIG. 2D, the cartridge is positioned slightly outside of the injector, and the jaw blades of gripper assembly 101 are expanded (open) for receiving the cartridge in the cartridge chamber 106. (Certain internal components of the injector are shown in cross-section FIG. 2D). FIG. 2D also shows a home run port 610. The home run port is the main connection point from the sensor block to the main processor using a single cable (instead of having several different wires connected to the sensors). Sensors 601, 602 are located on or within the needle-free injector. (In FIGS. 2A and 2C, sensor 602 is not shown as it is directly behind sensor 601). Jaw lock sensor 601 detects whether the jaws are open or closed at any given state. The software for this determines multiple times (e.g. per second) the state of the jaws: when a cartridge is inserted, to ensure that the cartridge is in position and locked; and after injection, determines that the cartridge has been used. When a cartridge is inserted into the needle-free injector, air cylinder actuator sensor 602 sends a signal to indicate that the cartridge is inserted: at that moment, a signal is sent from air cylinder actuator sensor 602 to air control valve (trigger valve) 701 (see FIG. 7). Air control valve 701 is connected to air-ports 627 and 629. Air is sent to air-port 629 to lock (close) the gripper assembly, whereas air is sent to air-port 627 to unlock the gripper assembly. Air is forced through the air-line 702 (see FIG. 7) to trigger the closing of the jaws by sending the air cylinder gripper 200 forward to cause the gripper jaw blades 104*a-c* to close around the cartridge; jaw lock sensor 601 then confirms that the jaws are closed. For example, when the jaws are open for receiving a cartridge, jaw lock sensor 601 is checked by the software to confirm that the jaws are open. Once the cartridge is inserted, and air cylinder actuator sensor 602 is activated, jaw lock sensor 601 is triggered again to detect and confirm that the jaws are now closed. The coupled signaling from jaw lock sensor 601 and air cylinder actuator sensor 602 help to prevent the premature release of the cartridge during use by ensuring that cartridge is in position, and that the jaws are locked.

Figure 3:
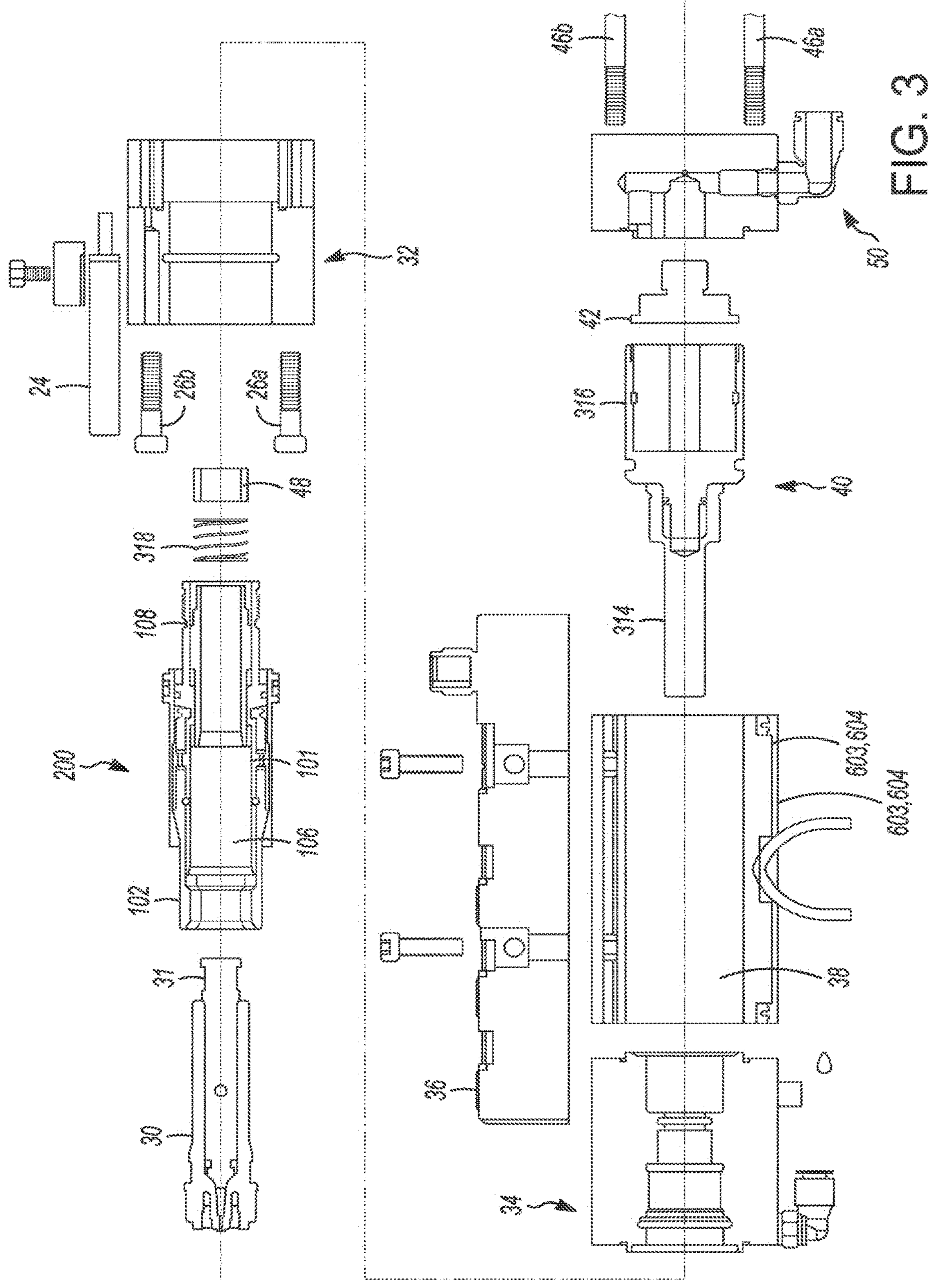
FIG. 3 shows an exploded view of a typical needle-free injector needle-free injector described herein, such as that shown in FIG. 1.
Figure 10A:
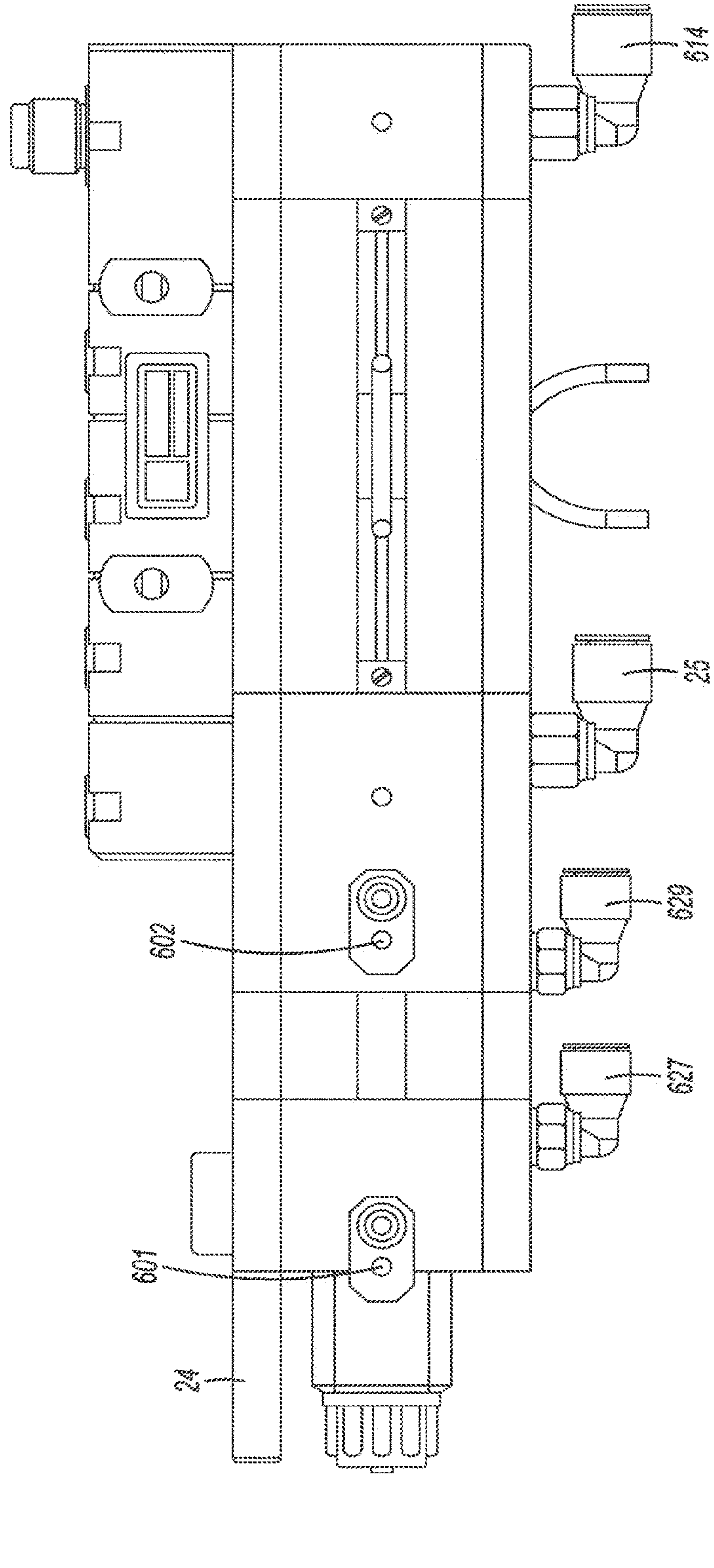
FIG. 10 shows side (FIG. 10A) and bottom (FIG. 10B) images of the needle free injector.
Figure 10B:
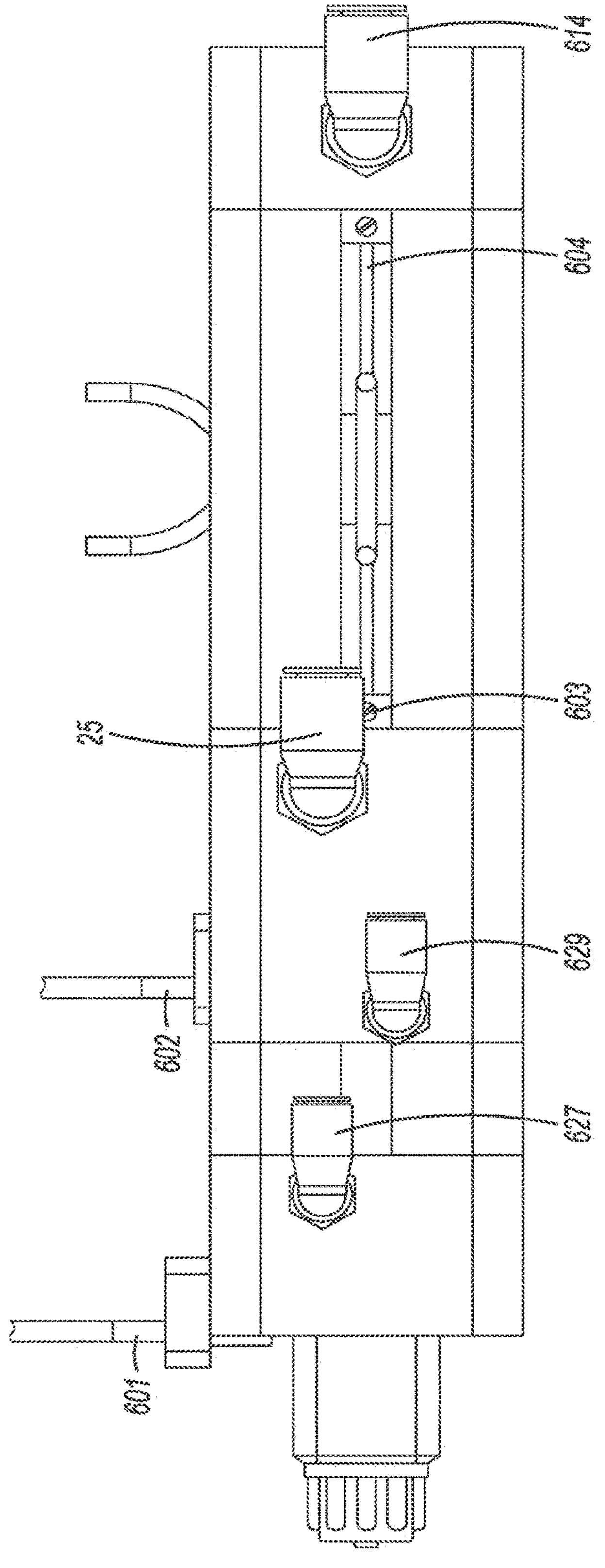
Figure 11:
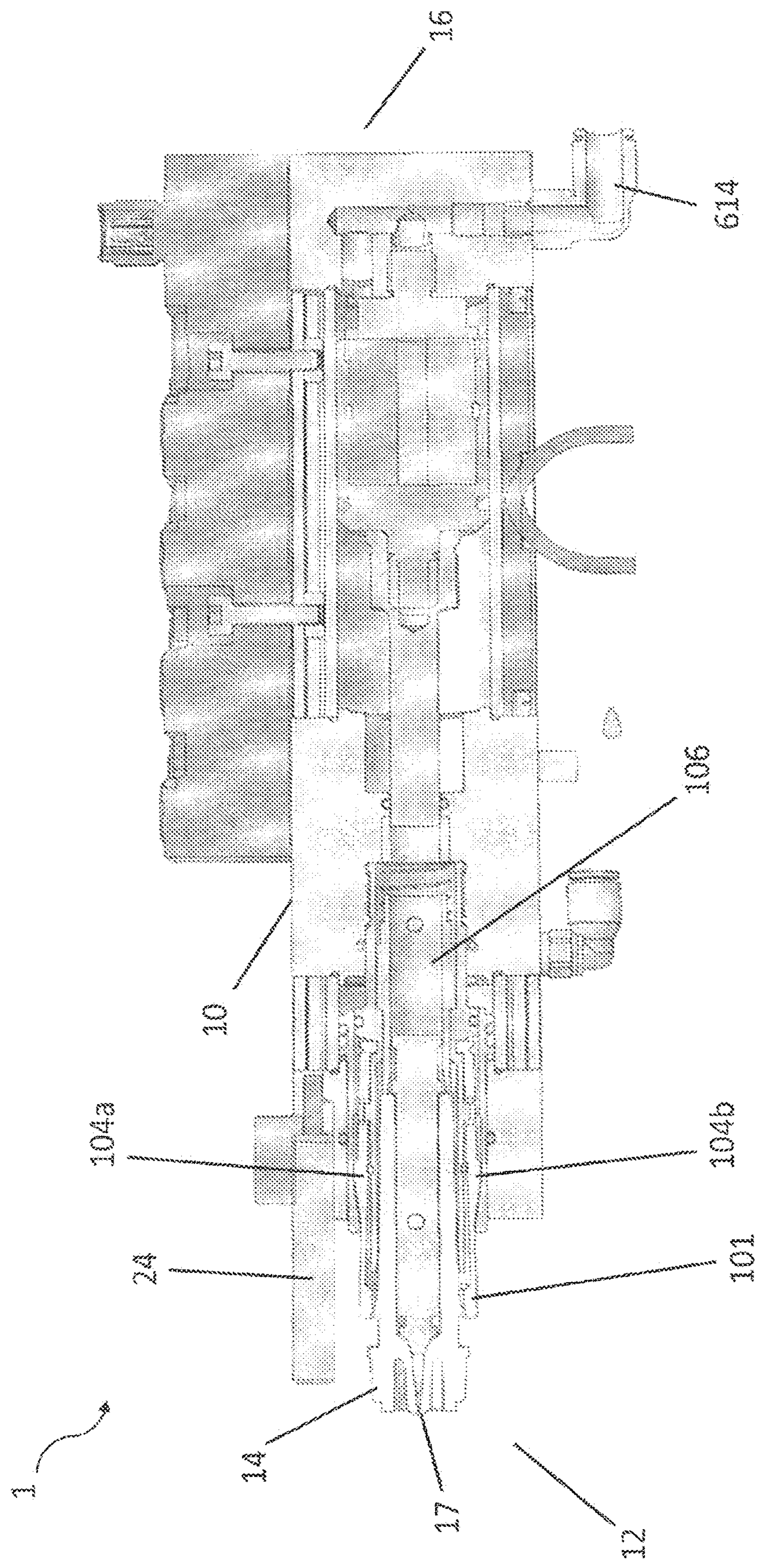
Figure 13:
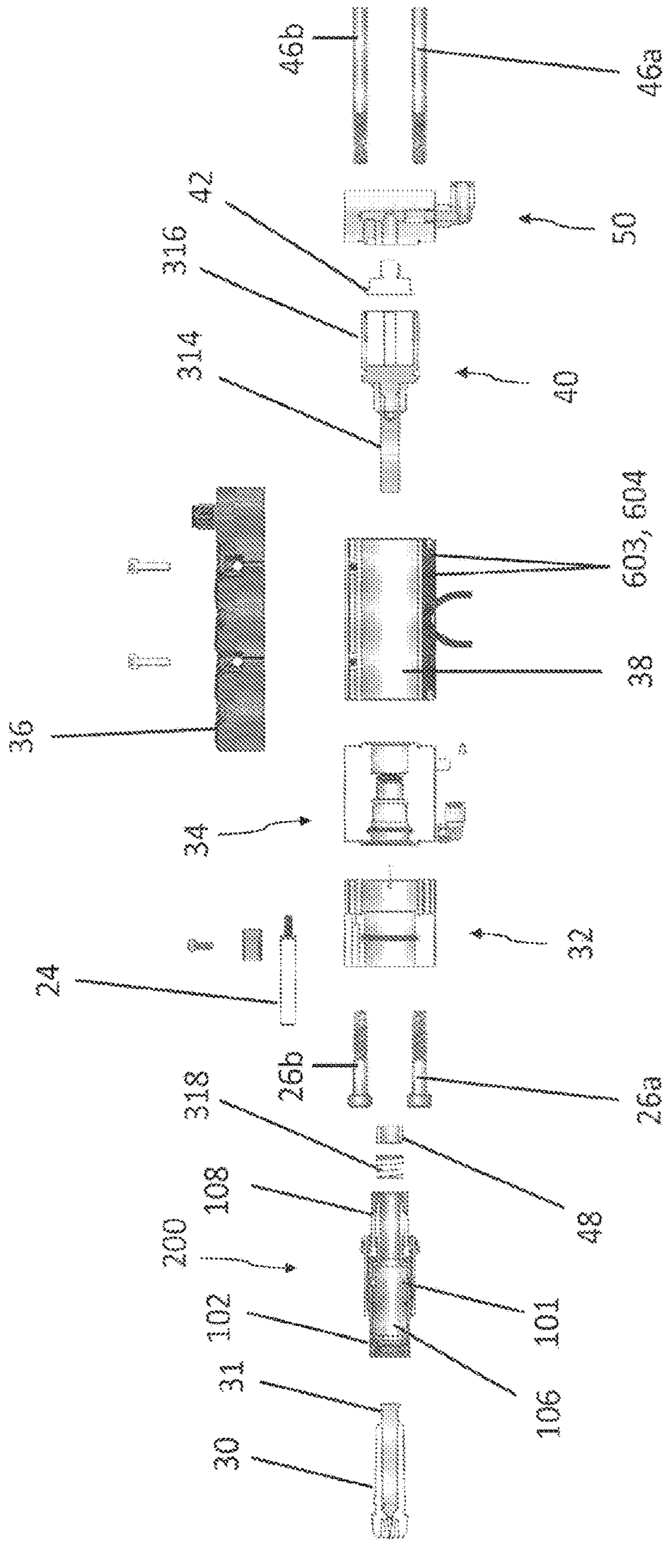
Figure 14:
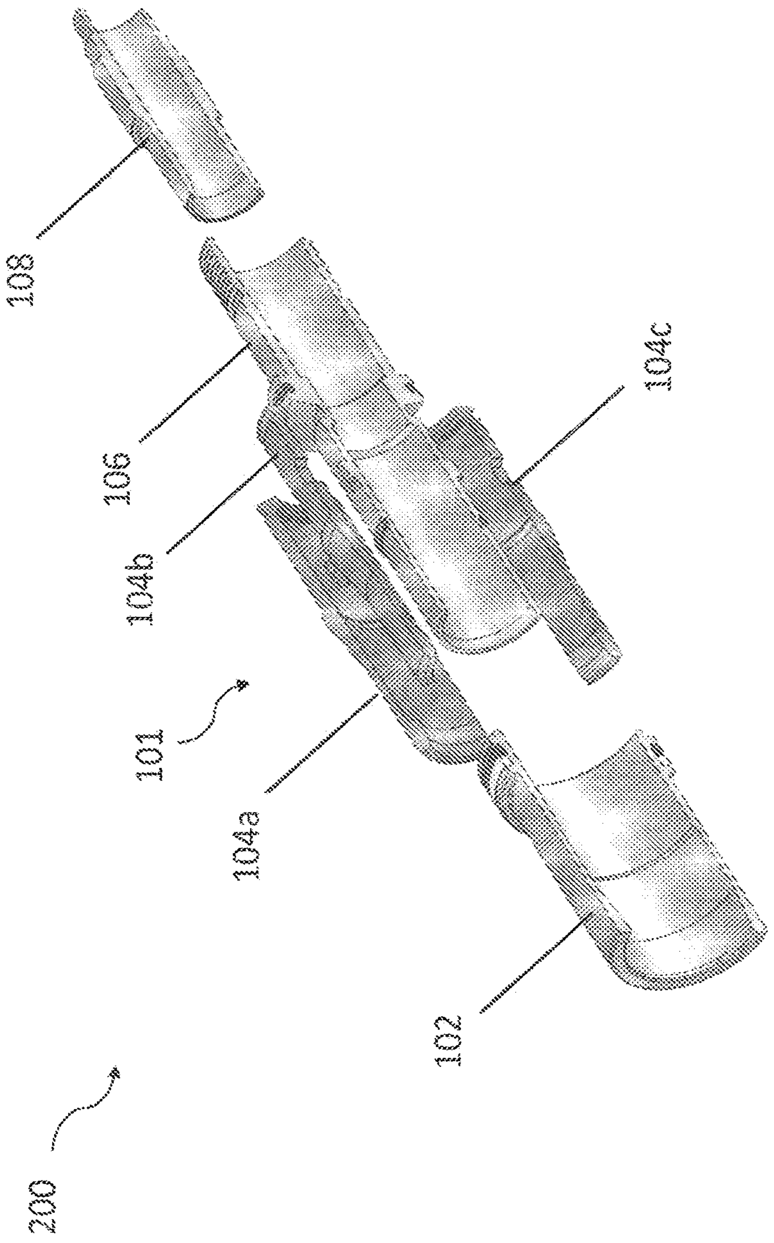
Figure 15B:
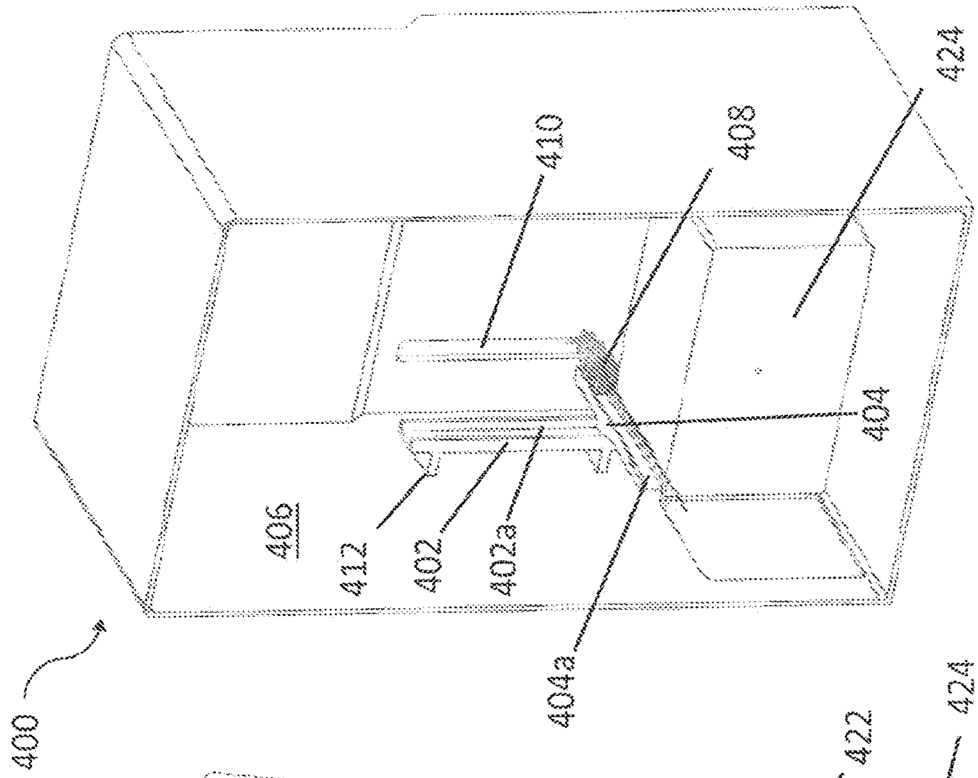
Figure 15A:
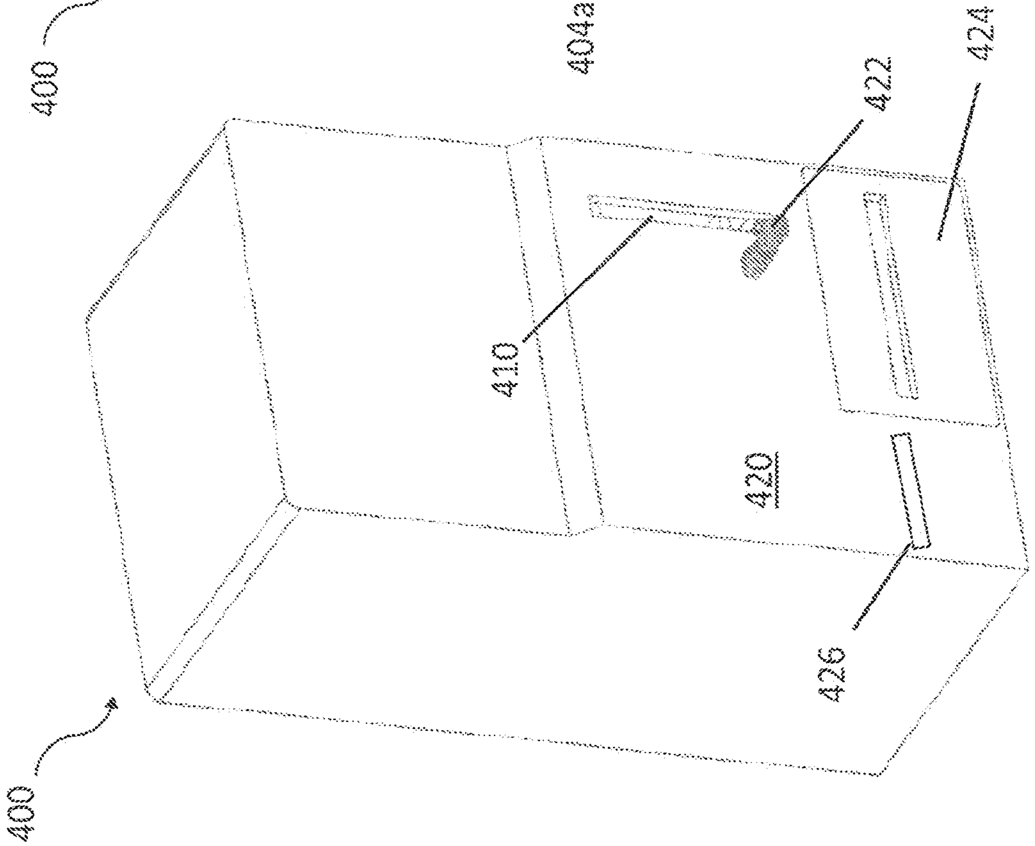
Figure 16:
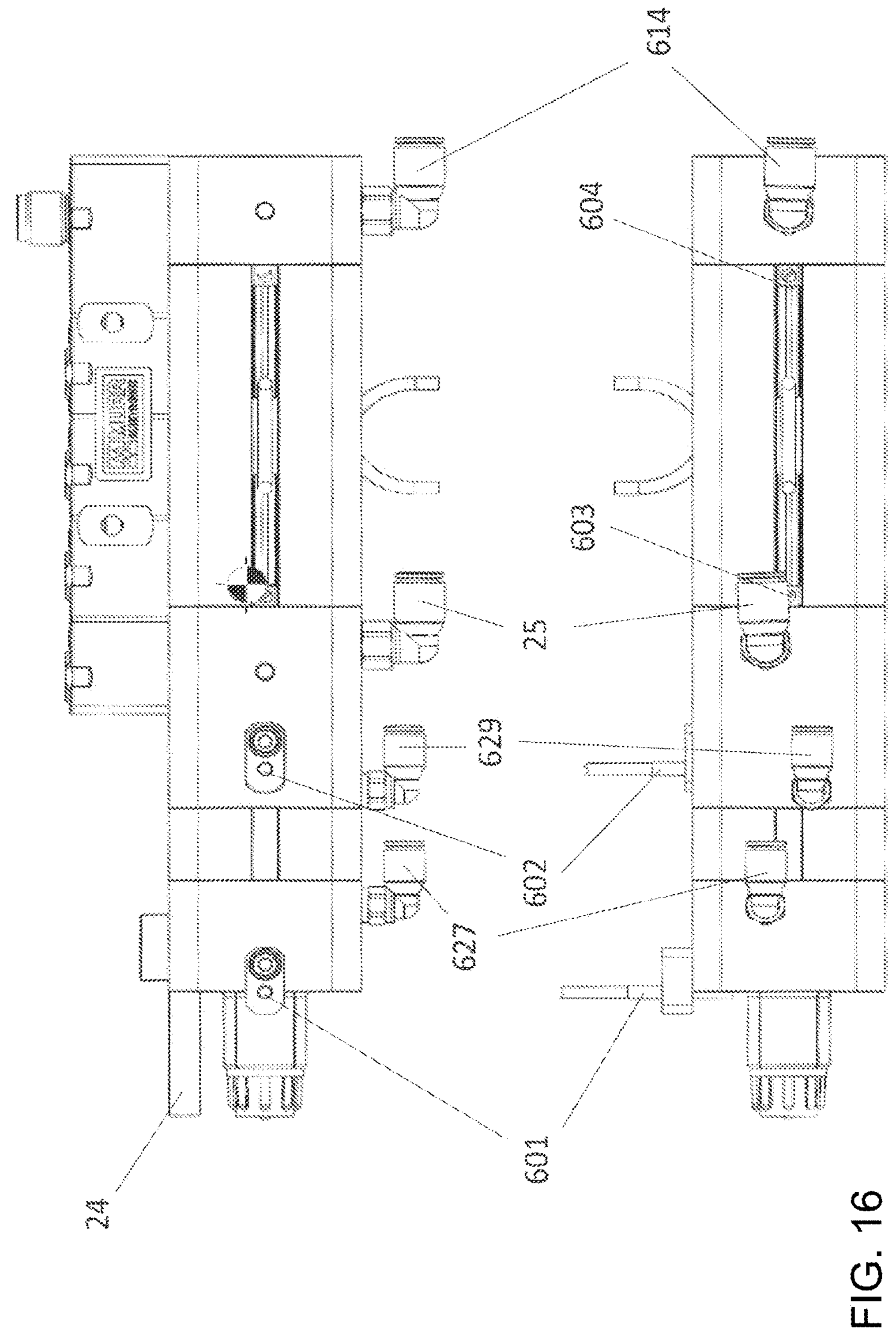

FIG. 3 shows an exploded view of the needle-free injector. The main cylinder 38 is provided which forms the central unit of the injector, coupled with the impactor assembly 40 that propels forward to impact the cartridge piston 31 of the cartridge assembly 30 to expel the medicament therefrom. Movement of the impactor assembly is modulated by linear impactor bearing 48. A cartridge such as the type described in U.S. Pat. No. 9,662,460 to Menassa, incorporated by reference herein, can be used. The cartridge is inserted into open cartridge cylinder 106 which is part of edge lock air cylinder gripper assembly 200 described in detail below. As also shown in FIGS. 10*a* and 10*b*, front housing block 32 holds the gripper assembly 200 and has an air-port lock 629 to close the grippers. In one embodiment, the cartridge comprises an edge lock ridge which substantially aligns with a front portion of the gripper jaw blades 104*a-c* that form the gripper assembly. The edge lock ridge comprises a larger diameter than the rest of the cartridge. This allows the gripper jaw blades 104*a-c* to hold the cartridge securely in place during the impact of the injection. A central housing block 34 holds the liner impactor bearing 48 and an air-port lock release 627 to open the grippers. An air-port injector return 25 is also present in the central housing block 34 to return the impactor to its home (retracted) position. The main cylinder 38 comprises magnetic sensors 603, 604 for sensing the position of the impactor assembly 40 within the main cylinder. The impactor assembly 40 towards the rear of the injector comprises a piston 314 and magnet 316. A rear housing block 50 comprises an air-port for effecting the injection motion. Assembly bolts 46*a*, 46*b* hold the injector and components at the rear of the injector.

To ensure that the cartridge remains in place (i.e., without being expelled from the cartridge holder prematurely), even if it is only half filled, a groove may be added to the O-ring on the back, adding a spring bias to the blade. In one embodiment, a groove depth of 0.5 mm, a groove bottom width of 0.5 mm, and with a 45-degree angle on both sides, is used. Thus, the present needle-free injector provides a quick release mechanism to ensure that the cartridge does not fly out undesirably from its cartridge chamber. As described above, two (or more) sensors in the injector detect position of the cartridge lock to confirm proper locking of cartridge.

FIG. 4 shows an exploded view of the edge lock air cylinder gripper assembly 200 used in a typical injector as described herein. Gripper cylinder 102 of the gripper assembly moves forward to close the gripper assembly 200 around the cartridge 30, or backward to open the gripper assembly 200 and release the cartridge 30. Central barrel 106 holds the cartridge. Surrounding at least a portion of the central barrel 106 is a gripper generally shown at 101, comprising three gripper jaw blades 104 (or more or less as needed) that constitute the gripper assembly. When a cartridge is added to the central barrel 106 in the injector, the barrel trigger 108 moves rearward within the injector. When the barrel trigger 108, at the rear (distal) end of the injector, is detected to be in contact with the air cylinder actuator sensor 602, the software detects that a cartridge is present in the injector; this sends a signal to move the gripper cylinder 102 forward, thereby locking the jaws around the cartridge and jaw lock sensor 601 confirms that the jaws are then locked. A spring 318 behind the gripper assembly assists with pushing the barrel trigger 108 forward as soon as the cartridge falls out after use, permitting air cylinder actuator sensor 602 to detect that the cylinder is empty (i.e. no cartridge). Jaw lock sensor 601 then detects that the Jaws are unlocked and ready to use for a next injection.

Figure 5:
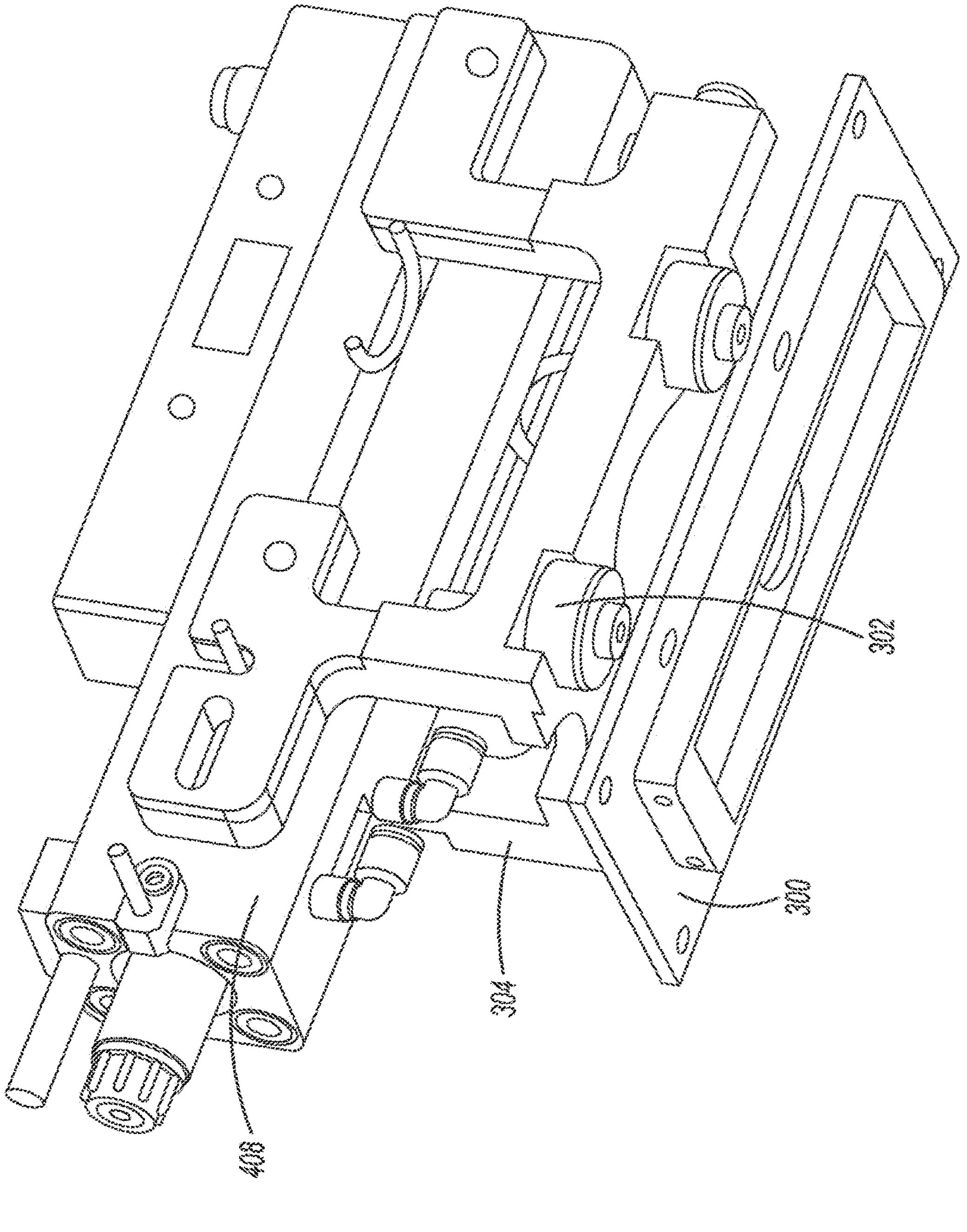
FIG. 5 shows an exemplary needle-free injector of the present application, such as shown in FIG. 1 or 2, secured to a movable platform in isolation, for use in the container unit.

FIG. 5 shows, in isolation, a needle-free injector 408 secured to a platform 300 which forms part of the robotic mechanism within the container unit (described below). The platform 300 supports the needle-free injector 408 and helps guide its movement within the container unit. The injector is attached to a brace unit 304 which is bolted to the platform 300. Rollers 302 or similar features may be added to the brace unit 304 to help smoothly guide the injector from its retracted position into use.

For automatic administration of vaccine, the needle-free injector is installed within a container unit. In this regard, a container unit as described herein may refer to any fixed or portable structure, such as a standalone box unit, self-contained or uncovered. The container unit may be connected to, or part of, a larger structure such as a kiosk or the like; the container unit itself, or peripherally to it, may comprise a computer having a user interface (e.g., touch-screen, keypad, and may include a television monitor which provides an instructional video, or video linkage to a remote location etc.) and sufficient equipment for a user to perform an injection. A video camera may also be included; this can be used for allowing a medical professional linked to it to view the vaccination and offer assistance in real time, if required. In the context of the present application, the container unit may be connected to or integral with a self-contained (enclosed) room or building, such as a hut, cubicle, locker, or other like structure which may be located within another structure, such as a pharmacy, hospital, or other commercial building. Ideally, the container unit may be part of an enclosure to provide privacy for the user and their pet, and may contain a door or curtain for privacy. In certain embodiments, the container unit comprises or is connected to a vaccine dispenser medicine cabinet or locker, preferably refrigerated, in which medicaments are securely stored, preferably locked therein.

Typically, the container unit comprises a computer to facilitate the different aspects of the vaccination process. For example, the computer may comprise a (graphical) user interface (such as a touch screen) which permits the customer to perform a number of functions, including but not limited to, accessing vaccination records, selecting a vaccine according to an immunization schedule, purchasing the vaccine, and updating the records after the vaccine has been administered. The computer also controls the operation of the robotic arm for extending, aligning the injector in use, and retracting the injector within the container unit for future use.

Figure 6B:
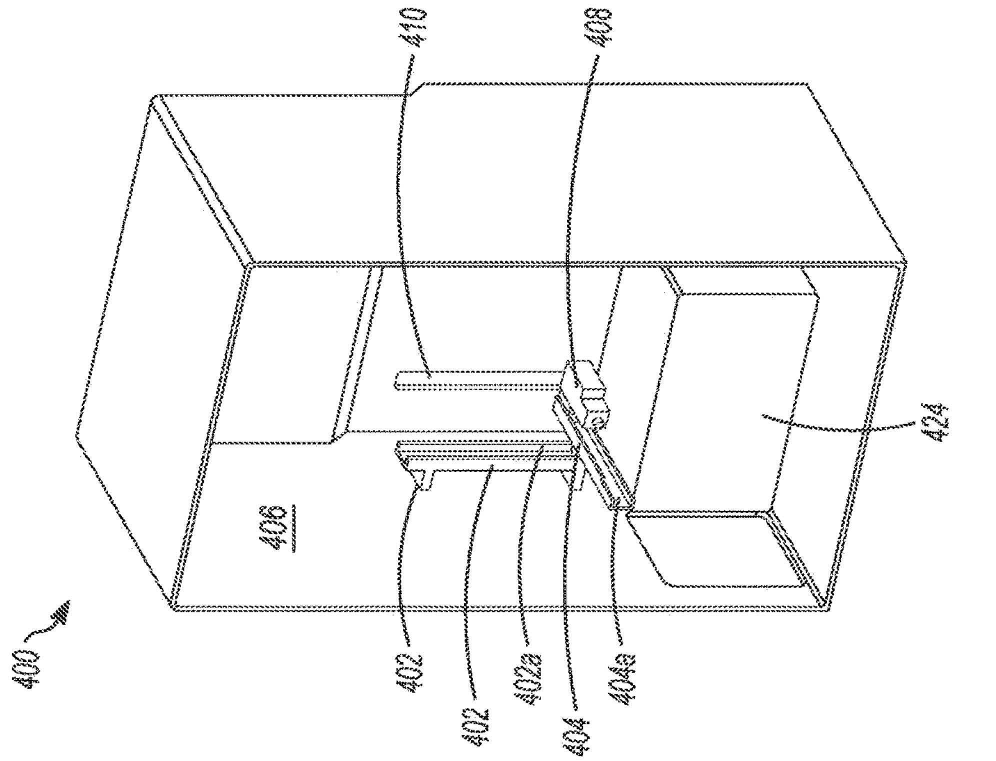
FIG. 6B shows a perspective rear view of said container unit.
Figure 6A:
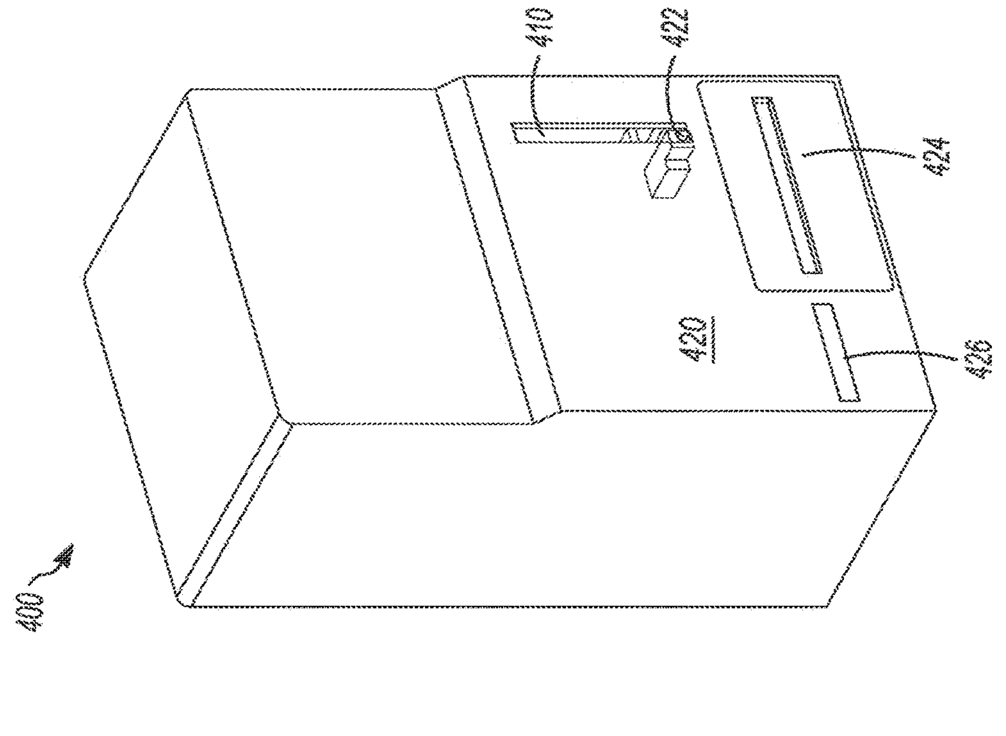
FIG. 6A shows a perspective front view of the container unit.
Figure 9:
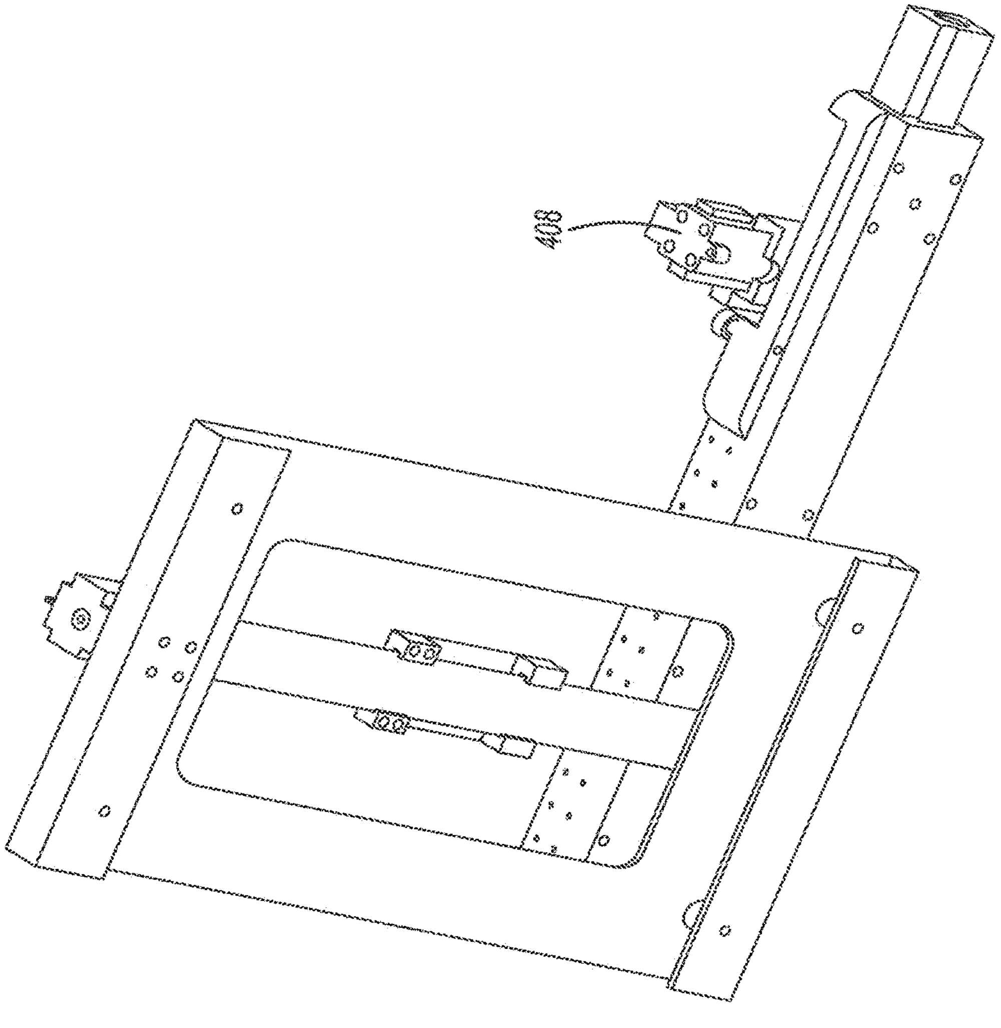
FIG. 9 shows the needle-free injector attached to a horizontal arm of the robotic assembly in the container unit, the injector aimed downward.

FIG. 6A (front view) and 6B (rear view) show one embodiment of a container unit as described herein. The container unit generally comprises an enclosed body 400 for supporting the needle-free injector attached to the robotic arm mechanism, and the related electronics and associated parts. FIG. 6B illustrates a rear view of the interior of the enclosed body 400. Vertical support arm 402 is secured to an interior panel 406 by one or more brackets 412, and is connected to horizontal injector arm 404 which supports the injector platform on which the injector 408 is retained. Either or both of the vertical support arms 402 and horizontal injector arms 404 comprise a channel 402*a* and 404*a*, respectively. These channels facilitate movement of the platform comprising the injector in horizontal (towards and away from the user) and vertical directions. The horizontal injector arm comprises a wheel which engages with an external surface of the injector. When the injector moves from the back (home) position to the injecting position, a front part of the injector body is contacted with the wheel, causing the injector to tilt upwards such that the injector is now horizontal and ready to inject. As it moves forward towards the opening in the front panel 420, the injector is positioned within a guide to keep it horizontal. In one embodiment, the injector is movable within the horizontal arm guide, and the whole horizontal arm is controlled by the vertical arm. When the injection is complete, the injector retracts along the horizontal arm, disengages from the horizontal arm guide, and allows the injector to tilt downward (rotate) by gravity. FIG. 9 illustrates the injector 408 pointed downward within the horizontal arm.

A slot 410 is provides an opening in the front panel 420 of the container unit. The slot 410 permits the injector tip 422 of the needle-free injector 408 to extend through the front panel 420 for access by the customer to vaccinate their animal. The slot 410 may be enlarged or elongated to a shape of size (such as the example illustrated in FIGS. 6A and 6B), to permit the injector to be moved up or down (or other orientation as provided and described above) by the horizontal injector arm 404 to accommodate animals of different sizes, or for injecting an animal at a preferred location on their body. While any suitably sized or shaped opening may be contemplated, an opening at least of a size to permit the injector tip to extend beyond the front panel for use by the customer is required for proper use of the needle-free injector. Ideally, the slot should have a cover or barrier on or within it to protect the user, the injector and the internal mechanism within the container unit. At least a part of the slot is open during the vaccination process, particularly restricted to the portion of the slot where the injector tip is exposed. Any suitable barrier or covering may be used, such as rubberized blocker or the like.

Access to the interior should ideally be limited; for example, a back panel (not shown) enclosing the container unit may comprise a door or other opening having a locking mechanism providing restricted access to a technician or the like. Thus, the injector mechanism is preferably locked or otherwise restrained in the container unit, such that it is inaccessible to a customer to reduce the likelihood of tampering that may damage the mechanism, or physical injury that may occur with improper use of the mechanism.

Figure 8:
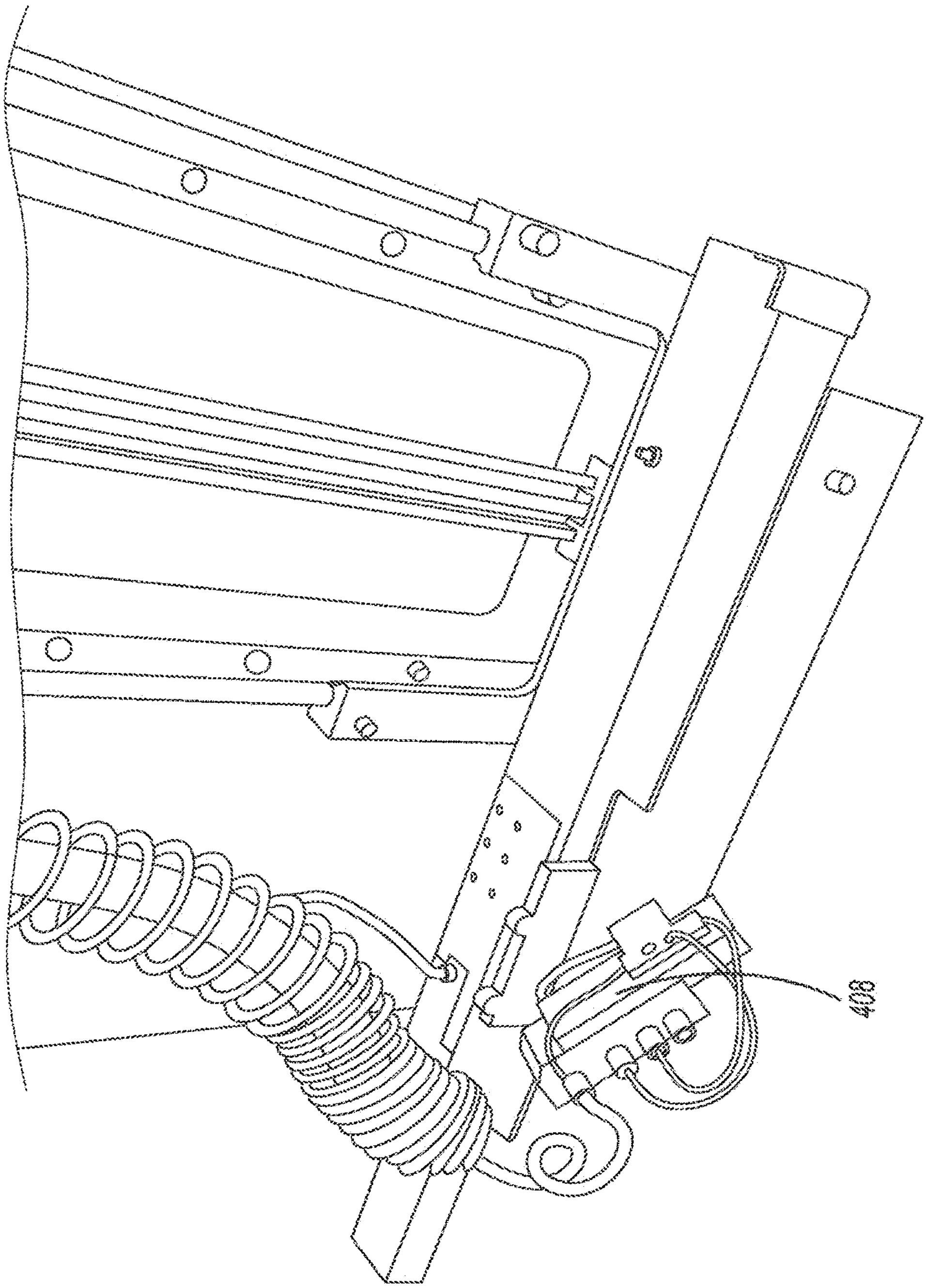
FIG. 8 shows a view of a section of the horizontal injector arm and needle-free injector of the container unit.

The injector mechanism is electrically connected or may be connected wirelessly (e.g., via a remote app, etc.) to a computer (not shown) having a processor which controls the movement of the robotic arm mechanism within the container unit. The processor ensures that the injector mechanism, comprising the needle-free injector and the robotic arm mechanism, are properly controlled and secured within the container unit. For example, the process of injection provides that the mechanism will move the injector tip 422 of the injector 408 out of the slot 410 on the front panel 420 for injection, then controls the movement to retract the injector 408 back inside the container unit 400. This movement may be programmed depending on the information pertaining to the pet to be vaccinated (i.e. based on information entered by the user on initiating the injection process). Once retracted, the injector 408 is tilted downwards by gravity as described above, such that the expended cartridge falls into a waste compartment (not shown). This is best illustrated in FIG. 8 or 9, whereby the injector is tilted downward. The robotic arm mechanism may be designed to move not only along the Z-axis (up or down) or Y-axis (forward and backward), but may also be rotatable about any of the X, Y and/or Z axes as required. If necessary, a user may override the system in cases of emergency, or to manually adjust the injector depending on the size of the animal.

Figure 7:
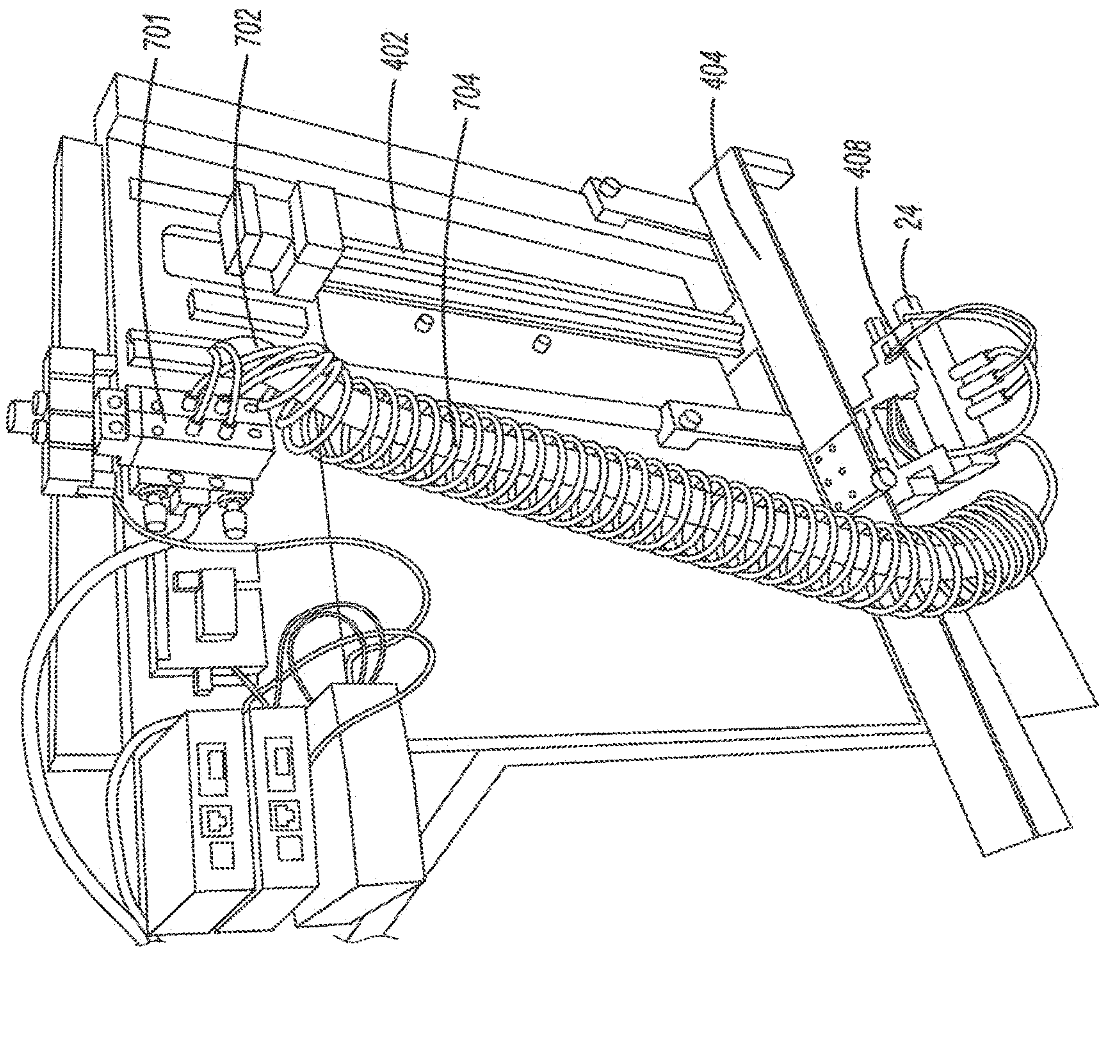
FIG. 7 shows a view of an interior panel of the container unit.

FIG. 7 illustrates the panel of the injector container unit, such as shown in FIG. 6. An air control valve 701 is shown which controls the air system from a compressor for injections from the cartridge in the injector 408. The various mechanical arms are provided on the horizontal axis 404 and vertical axis 402.

An animal platform 424 such as a step drawer may be present which may be part of, or connected with, the container unit, such as in a kiosk which houses the container unit. The animal platform may be used to place the animal to be vaccinated thereon for ease of administering the vaccine. Such an animal platform would ideally be placed abutting the front panel 420 of the container unit, or movable into or out of such position to allow for different sized animals to be injected.

A vaccine dispenser (not shown) within the container unit stores vaccines for use with the needle-free injector. A vaccine dispensing slot 426 is provided where stored vaccine cartridges (or other medicaments) are dispensed. The vaccine dispenser may be refrigerated to keep vaccines and other medicaments to be stored at a safe temperature, and is ideally locked to restrict access thereto.

Example

To gain a better understanding of the disclosure described herein, the following examples are set forth. These examples are for illustrative purposes only, and they should not limit the scope of the present application in any way.

In use, a customer (i.e., human user) approaches the container unit with their pet. Using the touchscreen interface on the computer connected with the container unit, the user enters in the appropriate information on their pet. This can include, but not limited to, the type of animal, the weight, size/length, vaccination history, family veterinarian, and age of the pet. Based on the software provided (or connection with a database on a remote server), the computer then provides a recommended vaccine (type, brand, dosage) and allows the user to purchase a cartridge of the vaccine from the vaccine dispenser for administration by the automatic injector. The user then enters their payment information (e.g., credit card, Interac®, cash, PayPal®, etc.) and, once approved, the vaccine dispenser dispenses a single-use vaccine cartridge. The cartridge containing the vaccine may be dispensed within a pouch or some other protective container, for added safety and to protect the integrity of the cartridge and its contents. Alternatively, the vaccine may be provided in a separate vial, either in the same pouch as a blank cartridge or in a separate dispensed pouch. A user can then transfer the contents of the vial (i.e., the vaccine) into the blank cartridge; this user-filled cartridge is then insertable into the injector.

The user then activates the injector by pushing a button or similar feature on the touchscreen. On command, the injector (which is located securely behind the front panel of the container unit) moves from its "home" position (i.e., with the injector retracted such that the injector tip is hidden and inaccessible to the user) into a vaccination position (i.e., where the injector is moved forward, towards the front panel, thereby exposing its injector tip to the user). The user then inserts the vaccine cartridge within an opening in the tip of the injector for holding the cartridge. As stated above, when the cartridge is inserted into the needle-free injector, air cylinder actuator sensor 602 sends a signal to trigger valve 701 (see FIG. 7), which in turn forces air through the air-line 702 to trigger the closing of the jaws by moving the gripper cylinder 102 forward to cause the gripper jaw blades 104*a-c* to close around the cartridge; sensor 601 then confirms that the jaws are closed around the cartridge. Ideally, a click or some other auditory indicator may be used to signal that the cartridge is locked and loaded. The vaccine is then ready for administration.

The user then places their pet on the animal platform adjacent the container unit, with the portion of their body to be injected abutted against the tip of the injector (i.e. at the dispensing end of the vaccine cartridge). The user has the option to move the injector up or down within the slot 410—by default, depending on the profile of the animal, the injector is moved automatically up or down into an appropriate position. However, the user may adjust this as needed, depending on the height of the specific animal to be injected. Once the animal is in position, capacitive contact sensor 24 on the injector (see FIGS. 2 and 10) detects the presence of the animal against the cartridge. In one embodiment, a countdown clock (or other visual or an audio indicator) may be provided on the computer screen or elsewhere in or on the container unit, advising the user that the injection is imminent. (Alternatively, the user may activate a button, such as on the touchscreen display, to indicate that the animal is in position). Ideally, the animal should be in contact with the contact sensor 24 for a period of time (typically about 3-5 seconds) before injection. In this pre-injection period of time, the user should attempt to keep the animal still and in position for injection. The contact sensor 24 determines that the animal remains in the proper position. After the pre-injection period, contact sensor 24 sends a signal to trigger valve 701 to fire the injector. In addition, the air-lines 702 for activating the jaws and locking mechanism, the trigger valve 701 further comprise injector air-lines 704 for moving the piston 314 (via the magnet 316) forward and backwards (see FIG. 3 for detail) to inject the vaccine. Specifically, the trigger valve 701 sends air from a compressor through the injector air-lines 704 causing the magnet and piston assembly to force the piston forward to against the cartridge. The vaccine is then injected from the cartridge. Magnetic sensors 603 and 604, towards the rear of the injector, detect when the magnet is forward (one of the sensors may be added as a failsafe against the other sensor, and a further sensor (not shown) may be added to the injector near the rear of the device to determine that the magnet is in a rear position).

Once the vaccine is injected into the animal, and the vaccination process is complete, the user removes the animal from the animal platform, and the whole injector unit (i.e. injector with platform 300 and brace unit 304) automatically retracts horizontally (and vertically as needed) within the container unit shortly after the injection (e.g. within about 1-2 seconds).

Once the injector is positioned back in its home position, the air control valve 701 sends air (through air-line 702) to air-port 627 to open the jaws of the gripper assembly. Sensor 601 confirms that the gripper assembly is open and sensor 602 confirms that the cartridge has fallen out of the injector (since the injector would, after having disengaged from the guide, would have tipped downward due to gravity), thereby discarding the empty cartridge into a waste bin (not shown). Ideally, the injector remains in the home position with the tip pointed downward, ready to use for a further injection. This is shown in FIG. 8. This position may reduce dust or other contaminants above the injector from falling in or collecting within the cartridge chamber.

FIGS. 11-16 show various aspects and embodiments of the present invention, generally corresponding to FIGS. 1-10, respectively.

The above disclosure and figures are intended to be illustrative and not exhaustive. The description will suggest many variations and alternatives to one of ordinary skill in the art. Those familiar with the art may recognize other equivalents to the specific embodiments described herein within, without departing from the spirit and scope thereof.

We claim:

1. An automatic needle-free injector container unit system comprising:

- a needle-free injector for injecting a medicament from a cartridge to a user, wherein the needle-free injector comprises a cartridge chamber for receiving the cartridge;
- an injector movement mechanism for automatically and reversibly positioning the needle-free injector to one or more of: a home position where injector is retracted and positioned away from contact with the user, and an injecting position where the injector is in proximity to the user for injection of the medicament; and
- a container for housing the needle-free injector and injector movement mechanism,
- wherein the needle-free injector comprises one or more sensors, wherein:

- a first sensor of said one or more sensors is a jaw lock sensor that detects whether a cartridge is locked into the cartridge chamber; and a second sensor of said one or more sensors is an air cylinder actuator sensor that detects when a cartridge has been inserted into the cartridge chamber.

2. The automatic needle-free injector container unit system of claim 1, further comprising:

a computer processor in connection with a user interface for controlling the needle-free injector and injector movement mechanism.

3. The automatic needle-free injector container unit system of claim 1, wherein the cartridge comprises the medicament for injection by the needle-free injector.

4. The automatic needle-free injector container unit system of claim 1, wherein the medicament is a vaccine.

5. The automatic needle-free injector container unit system of claim 1, wherein the needle-free injector comprises a cartridge gripper comprising one or more jaw blades, wherein on insertion of a cartridge within the cartridge sensor, the air cylinder actuator sensor triggers the one or more jaw blades of the cartridge gripper to grip around the cartridge to secure it within the cartridge chamber.

6. The automatic needle-free injector container unit system of claim 1, further comprising a third sensor of said one or more sensors which is a magnetic sensor that detects a position of a piston that moves forward when injecting the medicament from the cartridge.

7. The automatic needle-free injector container unit system of claim 1, comprising a horizontal arm having the injector thereon for moving the injector from the first position to the second position, and vice versa.

8. The automatic needle-free injector container unit system of claim 1, further comprising a lockable storage cabinet for holding medicament, whereby the container is temperature controlled.

9. The automatic needle-free injector container unit system of claim 8, wherein the medicament is a vaccine.

10. The automatic needle-free injector container unit system of claim 8, wherein the container is refrigerated.

11. The automatic needle-free injector container unit system of claim 1, further comprising a user interface in communication with the computer processor for allowing a user to input information on the user to be given the medicament.

12. A needle-free injector for injecting a medicament from a cartridge to a user, wherein the needle-free injector comprises a cartridge chamber for receiving the cartridge, for use with the automatic needle-free injector container unit system of claim 1.

13. A portable kiosk comprising the automatic needle-free injector container unit system of claim 1.

* * * * *